United States Patent [19]

Dixon et al.

[11] 4,085,158
[45] Apr. 18, 1978

[54] ISOAMYLENES FROM BUTENES

[75] Inventors: Rolland E. Dixon; P. Douglas Hann, both of Bartlesville, Okla.

[73] Assignee: Phillips Petroleum Company, Bartlesville, Okla.

[21] Appl. No.: 666,102

[22] Filed: Mar. 11, 1976

[51] Int. Cl.$^2$ ............................................. C07C 11/12
[52] U.S. Cl. .................... 260/680 E; 260/677 AD; 260/683 D; 260/683.15 D; 260/683.2
[58] Field of Search ....... 260/680 E, 683 D, 677 AD, 260/683.2, 683.15 D, 676 MS

[56] References Cited

U.S. PATENT DOCUMENTS

| | | | |
|---|---|---|---|
| 3,330,882 | 7/1967 | Albright | 260/683.15 |
| 3,364,278 | 1/1968 | Reusser | 260/683.15 |
| 3,445,541 | 5/1969 | Heckelsberg et al. | 260/683 D |
| 3,565,969 | 2/1971 | Hutto et al. | 260/683 |
| 3,592,868 | 7/1971 | Heckelsberg | 260/683.2 |
| 3,621,073 | 11/1971 | McGrath et al. | 260/680 D |
| 3,635,931 | 1/1972 | Davison | 260/683.2 |
| 3,642,933 | 2/1972 | Heckelsberg | 260/683.2 |
| 3,647,906 | 3/1972 | Farley | 260/683.15 D |
| 3,660,513 | 5/1972 | Davison | 260/680 E |
| 3,663,453 | 5/1972 | Myers | 252/441 |
| 3,723,561 | 3/1973 | Priegnitz | 260/677 AD |
| 3,763,261 | 10/1973 | Sobel | 260/683.2 |
| 3,810,955 | 5/1974 | Sobel | 260/683.49 |

Primary Examiner—Delbert E. Gantz
Assistant Examiner—Joseph A. Boska

[57] ABSTRACT

A feed of mixed butenes is separated by molecular sieves into a butene-1 stream and a stream comprising butenes-2 and isobutene. The butenes-2 and isobutene are disproportionated to yield isoamylenes. The isoamylenes can be converted to isoprene.

22 Claims, 2 Drawing Figures

ISOAMYLENES FROM BUTENES

FIELD OF THE INVENTION

The invention relates to a method of producing isoamylenes from a mixed butenes feed. In another aspect, the invention relates to a method for producing isoprene from a mixed butenes stream.

BACKGROUND OF THE INVENTION

Isoprene is an expensive monomer to manufacture, but highly desirable as a synthetic rubber feedstock. Not only are the polyisoprenes satisfactory for much the same uses as natural rubber, the polyisoprenes for many purposes actually are superior, being pure in composition.

Isoprene presently is manufactured, or recovered from various refinery streams such as naphtha cracker by-product streams, only in relatively limited quantities. Small amounts of isoprene are produced in ethylene plants, or can be recovered from by-product cracked gasoline produced by some ethylene plants. Some isoamylenes, precursors of isoprene, can be recovered from some cat cracker effluents and dehydrogenated to isoprene. Efforts have been made to produce isoprene by a by-product route involving propylene dimerization, but this has proven uneconomical.

Another source of feedstock that potentially could be useful in making isoamylenes by the triolefin disproportionation reaction has been the availability of various mixed butenes streams from such as a naphtha cracker $C_4$ stream of butylenes, or catalytic cracker effluent cut of butylenes. The stumbling block in any such approach has been the need to provide a balanced feed to the triolefin reaction of butenes-2 and isobutene without butene-1. Heretofore, efforts have been made in treating such mixed butenes streams to separate and purify each component, and then recombine butenes-2 and isobutene streams in a suitable proportion for disproportionation. These efforts have been costly, and prevented development of a suitable technology.

BRIEF SUMMARY OF THE INVENTION

We have discovered a process by which isoamylenes can be produced from a mixed butenes stream. We thus now are able to prepare isoprene readily and economically from a mixed butenes stream. Briefly stated, our invention comprises feeding a mixed butenes stream to molecular sieves wherein butene-1 is adsorbed, and butenes-2 and isobutene pass through to a triolefin (disproportionation) reactor for the production of isoamylenes. Other components produced in the disproportionation reaction, such as ethylene and propylene, are separated out. Unreacted butenes-2 and isobutene can be recycled to the disproportionation step. Our process includes optional though desirable steps. Ethylene formed in disproportionation can be separated and dimerized to form additional butenes. Butene-1 can be desorbed from the molecular sieves as an extract stream and either double-bond isomerized to butenes-2, or skeletally-isomerized to isobutene, or both. The isoamylenes produced can be dehydrogenated so as to produce the desirable and valuable isoprene monomer.

BRIEF DESCRIPTION OF THE DRAWINGS

Figure 1:
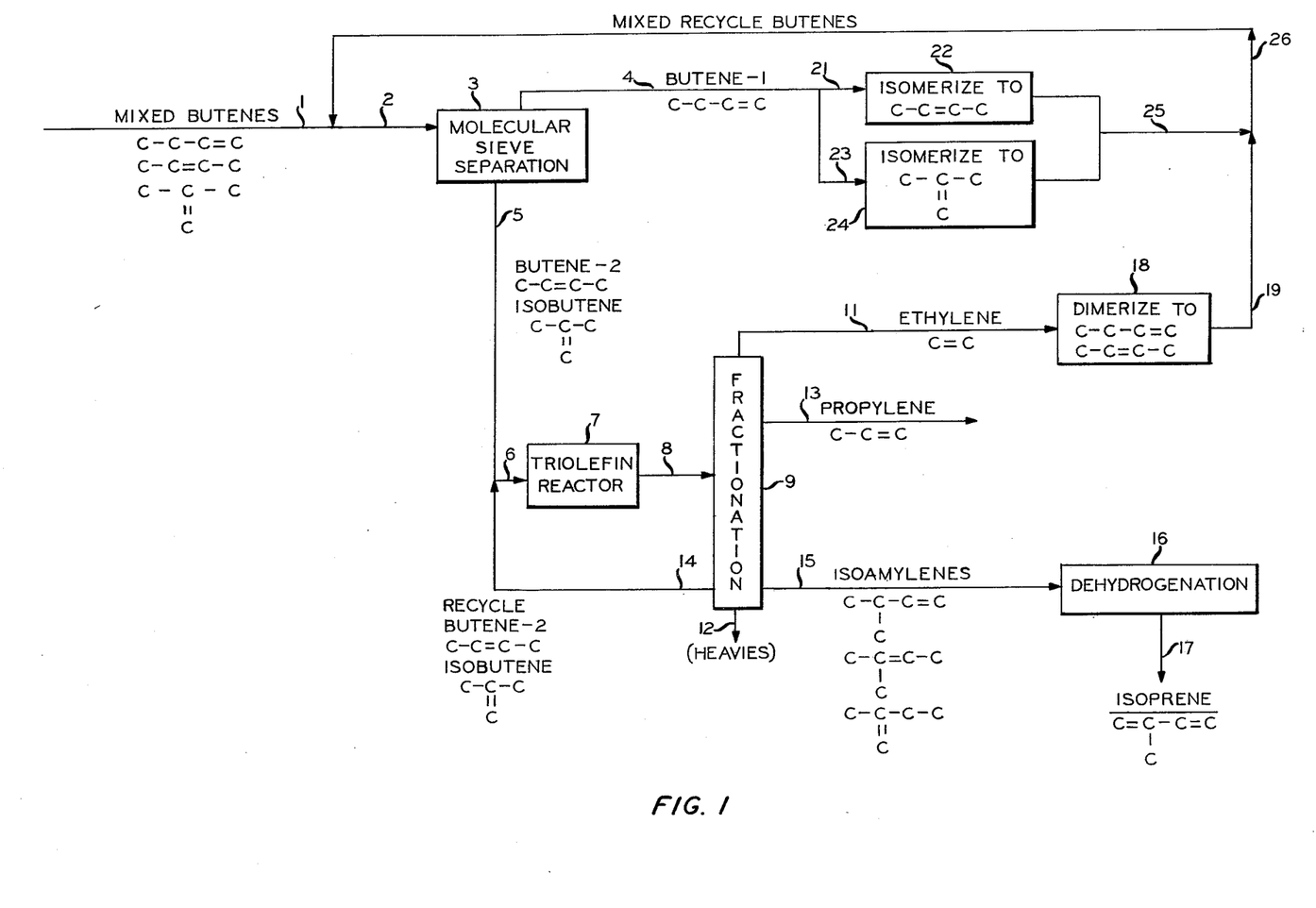

FIG. 1 presents a schematic overview of our process including several of the optional but desirable recycle and conversion steps. A feed 1 of mixed butenes are fed 2 to molecular sieves separation means 3. Butene-1 is adsorbed, while a stream 5 of butenes-2 and isobutene is passed through. The stream 5 of butenes-2 and isobutene is fed 6 to a triolefin reactor means 7 which converts the butenes-2 and isobutenes at least in part to isoamylenes. The reactor effluent 8 is subjected to separation means 9 to obtain the desired isoamylenes stream 15 which can be dehydrogenated 16 to isoprene 17. From the separation step 9, propylene 13 is separated for such uses as may be suitable, such as polypropylene; and ethylene separated 11 and can be dimerized 18 to produce additional butenes 19. A fractionation step (not shown) can be employed, if desired, to remove from stream 19 other than $C_4^=$ products, and the $C_4^=$'s then can be recycled 26, 2 to molecular sieve separation 3. Ethylene, if desired, optionally could be employed (not shown) for other purposes such as use in producing polyethylene.

The molecular sieves 3, which have adsorbed butene-1, on desorption release 4 the adsorbed butene-1 which can then be fed 21 to double bond isomerization means 22, or fed 23 to skeletal isomerization means 24, or in part to each, producing respectively additional butenes-2 and/or isobutene, in whatever proportions may be desired in order ultimately to balance the mixed feed 6 to the triolefin reaction means 7. Effluent 25 from the double bond isomerization 22 and/or skeletal isomerization 24 preferably is fed 26 back through 2 the molecular sieve 3 separation step, so that any unreacted butene-1 then is adsorbed and separated for recycle to isomerization, while the desired butenes-2 and/or isobutene become then a part of the mixed stream 5 and feed 6 to the triolefin reactor means 7.

Figure 2:
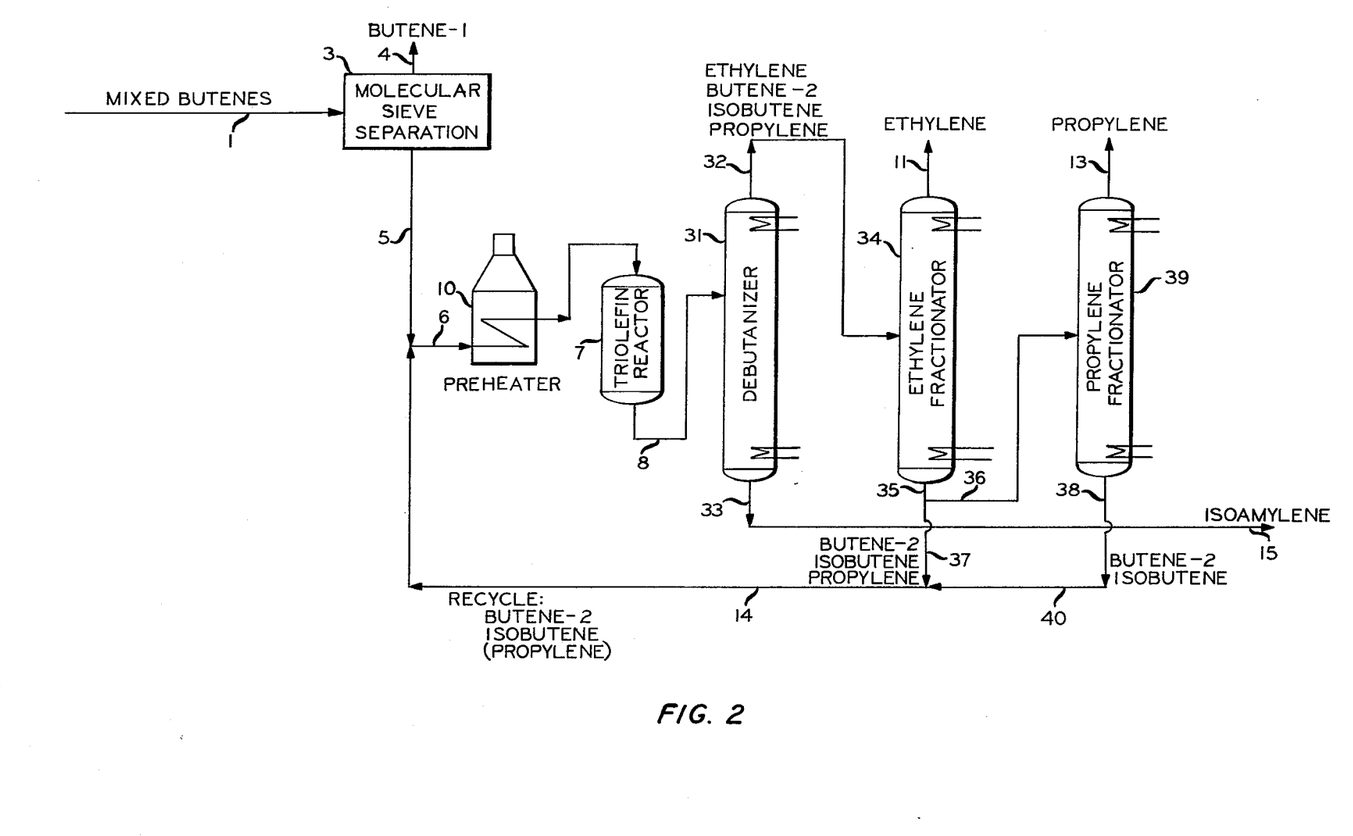

FIG. 2 is a view including a more detailed suggested separation step (9 in FIG. 1) for the effluent 8 from the triolefin reaction 7. In FIG. 2, the mixed feed 1 of butenes to the molecular sieves separation step 3 results in the passage therethrough 5 of a raffinate of butenes-2 and isobutene, while butene-1 is adsorbed. The raffinate stream 6 of butenes-2 and isobutene is preferably preheated 10 for disproportionation 7 resulting in formation of isoamylenes. Disproportionation effluent stream 8 contains ethylene as well as propylene, butene-2, isobutene, and isoamylenes. The disproportionation effluent stream 8 preferably is fed to a debutanizing means 31 for removal of isoamylenes and any heaviers as a bottoms stream 33, from which the isoamylenes 15 are readily separated by such as fractionation (not shown). The isoamylenes 15 then can be dehydrogenated to isoprene, as shown in FIG. 1.

The debutanizer 31 overhead 32 comprises at this point ethylene, if any, and propylene, isobutene, and butene-2. Where stream 32 contains ethylene, the debutanizer overhead 32 is fed to an ethylene fractionation means 34 which removes ethylene as overhead 11. Bottoms 35 from ethylene separation, or stream 32 where ethylene separation is omitted, comprising propylene, isobutene, and butene-2, then can be recycled 37, in whole or in part, to 6 the triolefin reactor 7; or can be, in whole or in part, preferably in part, sent 36 to a propylene fractionation means 39 for removal of propylene as overhead 13 to avoid build-up of propylene in the recycle system. Bottoms 38 comprising isobutene and butene-2 then is recycled 40, 14 to 6 the triolefin reactor 7. Ethylene overhead 11 from the ethylene fractionator 34 can be dimerized (see FIG. 1) to produce additional butenes for feed to the molecular sieve separation step 3 as before discussed. Propylene can be used, if desired, for a variety of purposes such as preparation of polypropylene, or can be codimerized (not shown) with a portion of the ethylene to produce additional isoamylenes which then can be combined with the isoamylenes from the olefin disproportionation for isoprene production.

DETAILED DESCRIPTION OF THE INVENTION

In accordance with the process of our invention, mixed butenes are separated by means of a molecular sieve separation step wherein butene-1 is adsorbed, and butenes-2 plus isobutene pass therethrough. These latter components subsequently are employed in a disproportionation step resulting in the formation of isoamylenes together with consequent formation also of some propylene, and generally to some extent some ethylene. The propylene, and any ethylene are separated from the isoamylenes The formation of linear amylenes C—C—C—C=C and C—C—C=C—C substantially is avoided when the feedstock is properly balanced in a suitable ratio of butenes-2 C—C=C—C and isobutene All of the isoamylenes can be readily dehydrogenated to form the desired isoprene, 3-methyl-1,3-butadiene, These formulae all are shown skeletally, for simplicity, without including the necessary hydrogen atoms attached to the carbons in appropriate locations.

From the triolefin reaction step effluent, unreacted butenes-2 and isobutene are separated by separation means for recycle to the disproportionation step. Ethylene, and propylene, also are separated from the reactor effluent stream. The ethylene can be dimerized to mixed butenes which then can be separated in the molecular sieve separation step. Propylene can be utilized for such uses as the formation of polypropylene, or can be codimerized with ethylene to form isoamylenes. Butene-1, desorbed, from the molecular sieve separation step can be double bond isomerized to butenes-2, or can be skeletally isomerized to isobutene, or a portion can be subjected to each such conversion, so as to provide desired proportions of butenes-2 and isobutene in the feed to the disproportionation step.

Mixed Butenes

The mixed butenes stream feed to the molecular sieve separation step comprises butene-1 C—C—C=C, butenes-2 C—C=C—C cis and trans, and isobutene Such a C$_4$= stream is readily available from a variety of refinery sources. Of course, such streams from any source generically, or from any particular plants individually, and from time to time, tend to vary considerably as to the relative proportions of butene-1:butene-2:isobutene.

While only the butenes-2 and isobutene are desired as members of a feed stream to a disproportionation step to be converted into isoamylenes, it is not practical to fractionate butene-1 from a mixture of butene-1 plus butenes-2 plus isobutylene. The relative boiling points at atmospheric pressure of some of these are close: butene-1 20.7° F., cis-butene-2 38.7° F., trans-butene-2 33.6° F., and isobutylene 19.6° F. Efforts at fractionation simply result in both isobutylene and butene-1 distilling overhead from the cis-butene-2 and trans-butene-2. In order to separate, recover, and ultimately recombine isobutylene with the butenes-2, the isobutylene heretofore has had to be separated by a process such as cold sulfuric acid extraction. This process step is economically undesirable and creates environmental problems in disposal of waste materials.

Where the feed of mixed butenes contains traces of nitrogen or sulfur-containing compounds, or acetylenics, pre-treatment prior to the molecular sieves step may be preferred. Refinery produced C$_4$ streams can be treated where necessary for removal of nitrogen- and sulfur-containing compounds by such as caustic washing followed by drying. Naphtha cracker C$_4$ streams containing acetylenes can be mildly hydrogenated. The naphtha cracker C$_4$ streams usually are very low in nitrogen and need no pre-treatment.

Molecular Sieve Separation

The sorbents which can be used in our process are those generally referred to as crystalline aluminosilicates or zeolites, including both the natural and synthetic aluminosilicates. The crystalline aluminosilicates can be described as having cage structures in which the alumina and silica tetrahedra are intimately connected in an open three-dimensional network. It is believed that the separation of the butene isomers is dependent primarily on electrochemical attraction of different isomeric configurations rather than upon physical size differences in the isomeric molecules. Therefore, there are no particular pore size limitations.

In hydrated form, exemplary crystalline aluminosilicates may be represented by $M_{2n}O:Al_2O_3 \cdot wSiO_2 \cdot yH_2O$ where M is a cation which balances the electrovalence of the tetrahedra and is generally referred to as an exchangeable cationic site, $n$ represents the valence of the cation, $w$ represents the moles of $SiO_2$, and $y$ represents the moles of water. The cations may be any one of a number of cations described hereinafter.

Suitable zeolites include the Type X and Type Y zeolites, as disclosed by such patents as U.S. Pat. Nos. 2,888,244 and 3,130,007, including those structures containing various cations exchanged upon the zeolite. The Type X zeolites can be represented in terms of mole oxides by $0.9 \pm 0.2\ M_{2n}'O:Al_2O_3:2.5 \pm 0.5\ SiO_2 \cdot yH_2O$ where M' represents at least one cation having a valence of not more than 3, $n$ represents the valence of M', and $y$ is a value up to about 9, depending upon the identity of M' and the degree of hydration of the crystalline structure.

The Type Y zeolites can be represented in terms of mole oxides for the sodium form by $0.9 \pm 0.2\ Na_2O:Al_2O_3 \cdot wSiO_2 \cdot yH_2O$ where $w$ is a value of greater than about 3 up to 8, and $y$ may be any value up to about 9.

Sorbents which may be utilized in the present invention include not only the sodium form of Type Y zeolites, but also crystalline materials obtained from such zeolites by partial or complete replacement of the usual sodium cation with other individual cations or groups of cations. Similarly, the Type X zeolites may also be ion-exchanged. Cations can be placed on the zeolite in any concentration ranging from about 1 to 100% of the original cations present. Cations which can be placed on the zeolite sorbent include the Group I-A, Group II-A, Group VIII and Group I-B metals of the Periodic Table of the Elements. Other cations not mentioned may be present in small quantities. Cations used on the sorbent can be selected from the above-mentioned groups such that the cation utilized is selective for 1-butene with respect to the other butene isomers. Of the above cations, potassium and barium presently are preferred for butene-1 selectivity and barium is especially preferred, since barium- and potassium-cation-containing zeolites selectively adsorb 1-butene over 2-butene and isobutylene.

In accordance with one step of our overall process, the mixed butenes feed including butene-1, cis-butene-2, trans-butene-2, and isobutene (isobutylene) is contacted with molecular sieves under conditions which separate the materials so as to provide a 1-butene stream and a stream comprising the butene-2 materials plus isobutene. Butene-1 is selectively adsorbed by the zeolite sorbent and is termed an extract material, leaving a raffinate comprising the butenes-2 and isobutylene. The extract material may also contain in some instances where small amounts of contaminants nitrogen- or sulfur-containing compounds in some instances where the original stream contained such and pre-treatment was not practiced. Where such are present, then the extract stream should be treated for removal of nitrogen and sulfur compounds by methods as described.

Sorption conditions include temperatures such as from ambient up to about 350° F. or higher, though temperatures less than about 300° F, more preferably about 50° to 150° F., are preferred. In some instances, higher temperatures such as 350° F. may be too high, since latent catalytic activity of the sorbent may cause some dimerization of the butene-1. Pressures can be of any reasonable range from vacuum up to hundreds of atmospheres, though presently pressures of about 200 to 250 psig are preferred. It is preferred to maintain sorption conditions to provide liquid phase contacting operation, although vapor phase operation may be utilized. Liquid phase operation includes the advantage of lower temperatures at given pressures, and the selectivity of the sorbent is enhanced for 1-butene at the lower temperatures.

Included in the separation operation, if desired, can be a purge step in which the raffinate material is purged from the sorbent by another hydrocarbon material or by a gas, leaving the sorbent containing 1-butene. Desorption removes the selectively adsorbed butene-1 from the sorbent. While vacuum desorption can be employed, more usually desorption includes passing a gaseous or liquid material through the sorbent in the substantial absence of the raffinate material and recovering the extract material by purging the extract material from the sorbent or replacing it by the desorbent. Useful desorbent materials include higher molecular weight $C_5$-$C_{15}$ olefins such as 1-octene which are later easily separated from 1-butene by such as fractionation. Desorbents which contain mixtures of normal olefins and isoparaffins also can be used. A presently preferred desorbent for 1-butene desorption in liquid phase operation comprises a mixture of about 20 volume percent 1-octene and 80 volume percent isooctane. Other normally liquid desorbent materials can be used, for example, the paraffins higher boiling than butene-1. Conditions for desorbing 1-butene include the pressure and temperature limitations described for adsorption operations, though usually slightly higher desorption temperatures are employed than for adsorption.

The 1-butene is recovered in admixture with the desorbent material, and is passed into a simple fractionating or separating means from which relatively pure 1-butene is recovered, and the separated desorbent reused in another desorption cycle. The residual desorbent material is removed from the sorbent by purging or vacuum treating operations. The sorbent can then be recontacted with the feed stock at sorption conditions appropriate for adsorbing 1-butene. Usually, two or more molecular sieve treating means are employed in parallel, so as to provide alternate desorption and thus continuing availability of butenes-2 and isobutene for disproportionation. Olefinic feed stocks which can be employed can contain from about a few percent 1-butene and a few percent total $C_4^=$ olefins content up to essentially pure $C_4^=$ olefins, with the balance saturated materials. Of course, the use of a feedstock of substantially pure $C_4^=$ olefins is preferred, for economical operation and a materials handling standpoint, though saturated diluents can be separated at any convenient point in the process. A specific olefinic reactant feed stock utilizable in our process contains about 35 volume percent butene-1, 32.5 volume percent isobutylene, and 32.5% butenes-2. Another suitable composition is a feed stock containing approximately 21 volume percent butene-1, 21 volume percent isobutylene, 32 volume percent butenes-2, with remaining feed stock components comprising paraffinic hydrocarbons.

Disproportionation

Triolefin Reaction

In the disproportionation step of our process, an admixture of the butenes-2 and isobutylene is disproportionated to yield isoamylenes and propylene, and usually some by-product ethylene. The disproportionation sometimes is termed the "olefin reaction" which can be visualized as comprising the reaction between two first pairs of carbon atoms, the two carbon atoms of each first pair being connected by olefinic double bond, to form two new pairs from the carbon atoms of said first pairs, the two carbon atoms of each of said two new pairs being connected by an olefinic double bond.

It is presently preferred that the feed to the olefin disproportionation step represent a mole ratio of isobutylene:butenes-2 of the order of about 1:1 for optimum production of isoamylenes. However, a broad ratio of excess of one to the other can be tolerated, since unreacted material can be separated and recycled. Also, our overall process provides for internal adjustments in order to provide for a balanced mole ratio by isomerizing separated butene-1 to either butenes-2 or isobutenes; and/or by dimerizing produced ethylene to butenes. Where the butenes-2 proportion is low, as it may be in some feedstocks, the recycle of produced propylene, or even admixture of moderate amounts of propylene from an outside source, can be used to balance the necessary feed ratios, since, in effect, propylene can replace butenes-2 on a mole for mole basis. Of course, as compared to butenes-2, propylene is a less desirable feed due to possible competing reactions.

Among the suitable catalysts are silica or thoria promoted by an oxide, or a compound convertible to the oxide by calcination, of tungsten, molybdenum, rhenium, or tellurium, or by a sulfide of tungsten or of molybdenum.

Other suitable catalysts include aluminum phosphate, zirconium phosphate, calcium phosphate, magnesium phosphate, or titanium phosphate, promoted by one or more of a sulfide of molybdenum or tungsten, or by an oxide or of a compound convertible to the oxide on calcination, of molybdenum, tungsten, or rhenium, or by magnesium tungstate or beryllium phosphotungstate. These catalysts can be in the form of a powder, or granules, as well as a variety of other shapes as is known in the art.

With a fixed bed reactor means in a continuous operation mode, temperatures presently preferred are in the range of about 650° to 750° F., employing a pressure in the range of about 200 to 350 psig, preferably close to about 300 psig, employing a weight hourly space velocity in the range of about 50 to 200, preferably about 75 to 100, weight/weight/hour.

The effluent from the triolefin reactor means step then is separated by suitable separation, usually fractionation, means. The reactor effluent comprises unreacted butene-2, unreacted isobutene, the desired isoamylenes one or more, propylene, and ethylene. Separation is effected to separate the ethylene, separate the propylene, remove preferably any heavies which may have been produced, separate butenes-2 and isobutene as a recycle stream back to the triolefin reactor means, and to obtain the desired product stream of isoamylenes. Typical exemplary conditions are discussed hereinbelow for each step, though operating conditions for fractional separation will be defined by a number of design restrictions such as cooling, water temperature, heating means, and the like.

Separation can be accomplished expeditiously by means of a first stage comprising a debutanizing means wherein the isoamylenes are removed as bottoms, and the remaining stream comprising ethylene, if any, together with propylene, butene-2, isobutene, is taken overhead. Typical operating conditions for such a debutanizer means include a suggested top temperature of such as about 170° F., bottom temperature of such as about 314° F., and an operating pressure of such as about 220 psia.

The overhead stream from the debutanizer means comprising ethylene, and propylene, isobutene, and butene-2, advantageously and conveniently can be fed to an ethylene fractionation means to remove ethylene overhead, and take the propylene and butene-2 and isobutene as bottoms. The ethylene fractionation means conveniently and typically can be operated at such as about −11° F. top temperature, 203° F. bottom temperature, and at an operating pressure of about 340 psia.

The separated stream containing propylene, isobutene, and butene-2 advantageously can be fed directly back to the triolefin reactor means, or can be preheated before feeding to the triolefin reactor means, or more preferably and advantageously the stream, at least in part, more preferably all of the stream, is treated for propylene separation. The amount of propylene recycled is determined by the stoichiometric requirements to balance with the isobutylene content since either butene-2 or propylene will react to form isoamylenes. Of course, undue excess propylene should not be recycled since this would tend to favor a competitive reaction, for example, formation of ethylene and butenes-2, which may necessitate further conversion, such as dimerization of the ethylene, and separation and recycle of the butenes-2.

In the propylene fractionation means, a convenient and presently preferred operating mode employs a top temperature of about 113° F., a bottom temperature of about 200° F., and an operating pressure of the order of about 274 psia, effective to remove propylene overhead, and provide a bottoms stream comprising the isobutene and butene-2.

The isoamylenes so produced then can be subjected to dehydrogenation to produce isoprene. This can be accomplished conveniently by oxidative dehydrogenation of the isoamylenes to isoprene. Conversion need not be quantitative, since any unconverted isoamylenes can be separated and recycled.

A catalyst particularly suitable for the necessary selective oxidative dehydrogenation of isoamylenes within the midst of other $C_5$ components is an iron-phosphorus-oxygen catalyst system prepared to have an excess phosphorus content of about 0.01 to 2 times, preferably about 1.05 to 1.5 times, the stoichiometric amount required for the phosphorus to react in the form of orthophosphate ions $PO_4^\equiv$ with all the iron in the catalyst. Such catalysts are highly active catalysts for the particular process involved in our invention. The iron within the catalyst composition can be ferric, ferrous, or a mixture of ferro and ferri forms.

Operating conditions for oxidative dehydrogenation can vary widely. Typical conditions include a temperature in the range of about 700° to 1300° F., preferably about 800° to 1200° F.; a pressure in the range of about 0.1 to 250 psia, preferably about 0.5 to 25 psia; an oxygen:gaseous $C_5$ feed volume ratio in the range of about 0.1:1 to 3:1, preferably about 0.5:1 to 2:1; and a steam:$C_5$ feed volume ratio in the range of about 0.1:1 to 100:1, preferably about 5:1 to 20:1. The $C_5$ feed space rate can be about 50 to 5000, preferably about 100 to 2500, volumes of feed vapor per volume of catalyst per hour.

The process itself ordinarily is carried out by forming a mixture preferably preheated, of the $C_5$ feed, steam, and an oxygen-containing gas, and then passing this admixture over the catalyst at the desired temperature and pressure relationships. The oxygen-containing gas can contain inert diluents such as nitrogen and the like as in air, or even can be flue gases containing residual oxygen. Pure or substantially pure oxygen is suitable.

The resulting stream from oxidative dehydrogenation then can be purified by means known to the art, such as by extractive distillation, which would produce an isoprene stream of desired concentration and purity for subsequent purposes such as polymerization.

Butene-1 Isomerization

The butene-1 desorbed from the molecular sieve separation step can be converted by double bond isomerization to butene-2, or by skeletal isomerization to isobutene, one or the other, or in part by each such transformation, as may be desired in accordance with the proportions of butene-2 and isobutene in the mixed butenes feed stream, so as to provide a stream of proper balance to the triolefin disproportionation reaction means step.

The olefinic feed stream can be diluted, if desired, though less preferably, with essentially inert diluents such as, for example, paraffins having 1 to 5 carbon atoms, or other gases such as nitrogen or hydrogen. The diluent can be present in any desired proportion such as, for example, about 5 to 95 weight percent of the olefinic feed stream. Such saturated diluents can be subsequently readily separated from the isomerized butenes by such as fractionation.

Butene-1 Double-Bond Isomerization

One convenient method of converting butene-1 by double bond isomerization to butene-2 is by contacting the butene-1 with a catalyst comprising ruthenium oxide. Preferably, the ruthenium oxide is associated with a suitable support material. Preferred supports include silica, silica-alumina, alumina, and titania. Excellent results are obtained when the support is silica. When the catalyst support is silica, any suitable catalyst grade silica can be employed. Some examples are precipitated silica gel, microspheroidal silica, flame hydrolyzed silica and silica aerogels. These materials have appreciable surface area, usually in the range of about 50 to 700 m$^3$/g, and can range from fine powders to coarse granules. These materials often contain small amounts of other compounds, including for example, amounts of alumina and sodium in the order of a few tenths of a percent by weight and smaller. Amounts of these and other materials which do not substantially prevent the desired reaction or unduly promote side reactions are acceptable.

A sufficient amount of the ruthenium oxide is used to obtain the desired activity. Because ruthenium oxide usually is more expensive than the support material, unnecessarily large amounts ordinarily are not used. Generally, the catalyst composite contains about 1 to 15, preferably about 2 to 10, weight percent ruthenium oxide calculated as RuO$_2$, and can be prepared by any suitable method of catalyst preparation, preferably by impregnation. Before use, the catalyst composite can be activated or regenerated by contact with flowing air at elevated temperatures at a time sufficient to produce the desired activity. Activation temperatures in the range of about 800° to 1200° F., for times ranging from about 0.1 to 24 hours, are suitable.

Exemplary conversion temperatures lie in the range of about 200° to 700° F., at any suitable pressure, preferably temperatures in the range of about 300° to 600° F. Pressures in the range of about 0 to 2000 psig, for example, can be used. The space rate for continuous operation usually will be in the range of about 5 to 15 parts by weight of feed per part by weight of catalyst per hour. After reaction, the reaction mixture can be separated as desired and unconverted materials recycled to the reaction zone.

The process can be carried out by any suitable contacting technique, either batchwise or continuously, using such as a fixed catalyst bed, stirrer equipped reactor, or other mobile catalyst contacting process.

Butene-1 Skeletal Isomerization

When it is desired to convert all or a portion of the butene-1 by skeletal isomerization to isobutene, any means known to the skeletal isomerization arts can be employed. One convenient means for converting butene-1 to isobutene employs an activated catalyst of zirconium oxide, or compound convertible to zirconium oxide upon calcination, preferably promoted by a halogen compound. A presently preferred example can be represented by ZrOX$_2$ wherein X is fluoride, bromide, chloride, or iodide, on alumina. Of these, presently the zirconyl chloride is more preferred. Of the aluminas, presently preferred are eta- and gamma-alumina, and presently most preferred is eta-alumina. A suitable and exemplary catalyst can be prepared by incorporating about 0.4 to 15 weight percent, preferably about 1 to 10 weight percent, based on the total composition, of zirconyl halide into the selected alumina, such as by impregnating a dried and calcined alumina with an aqueous solution of the desired zirconyl halide, followed by calcination at suitable temperatures such as about 500° F. to 1200° F. for a time such as about 0.1 to 25 hours, in air, or other gas such as nitrogen.

The skeletal isomerization step can be carried out by contacting the feed with the catalyst, using any suitable contacting techniques, at a suitable temperature at which skeletal isomerization of the feed olefin will occur. The temperature preferably is in the range of about 400° to 1200° F. or more, preferably about 600° to 1100° F. The liquid hourly space rate generally will be in the range of about 0.1 to 50, preferably about 0.5 to 30. Any convenient pressure can be used, with the lowest practical pressure preferred in order to minimize side reactions such as polymerization. Pressures ranging from atmospheric to such as about 200 psig are particularly suitable.

Ethylene Dimerization

Ethylene, which can be produced in the olefin disproportionation step in small or major amounts, depending upon the feed composition, and has been separated from the triolefin step reactor effluent, can be utilized otherwise in the modern refining and chemical conversion complex frequently termed a petrocomplexity, such as in the preparation of polyethylene. Optionally, and preferably in accordance with one aspect of our overall scheme, the ethylene is utilized within our process by dimerizing the ethylene to produce additional butenes, butene-1, butenes-2, and isobutene.

Typically, and presently preferably, the ethylene can be converted to butenes in high yield by means of a catalyst comprising the product resulting from admixing an organoaluminum compound with a complex of cobalt with a beta-diketone. The reaction of the beta-diketone complex of cobalt with the organoaluminum compound can take place over a wide range of temperatures; however, the reaction temperature generally will range from about 0° C to 200° C. The reaction time is quite short, generally on the order of a few minutes. The mole ratio of the organoaluminum compound to the cobalt complex, although it too can vary widely, typically will be in the range of about 2:1 to 100:1, preferably about 2:1 to 10:1.

Preferred combinations of the above organoaluminum compounds and beta-diketones include diethylethoxyaluminum and acetylacetone, diisobutylethoxyaluminum and acetylacetone, diethylmethoxyaluminum and acetylacetone, diisobutylmethoxyaluminum and acetylacetone, diethylethoxyaluminum and 2,4-hexanedione, diisobutylethoxyaluminum and 2,4-hexanedione, and diisobutylmethoxyaluminum and 2,4-hexanedione. A presently preferred combination is cobalt acetylacetonate and diethylethoxyaluminum.

The method of conversion of ethylene to butenes can be carried out by contacting ethylene with the catalyst system under reaction conditions including an inert hydrocarbon diluent such as n-hexane, n-heptane, isooctane, cyclohexane, methylcyclohexane, benzene, toluene, xylene, and the like. The conversion can be carried out at exemplary temperature in the range of such as about 0° C to 200° C., preferably about 25° to 125° C., more preferably about 30° C. to 60° C., employing autogenous pressures which can range as high as several thousand pounds per square inch depending upon the reaction temperature and diluent, though pressures of about 500 to 800 psig are presently preferred. The reaction time can vary widely, such as from less than 1 minute to about 10 minutes, but can be as long as several days. The amount of catalyst employed can vary over a wide range, but typically is in the range of about 0.5 to 10 weight percent total catalyst based on the mixture of catalyst system and diluent.

The butenes so produced, comprising butene-1, butenes-2, and isobutene, together with any unconverted butene-1, can be recycled to the molecular sieve separation step.

EXAMPLES

The examples are intended to assist in understanding of our invention, and not to be limitative of the reasonable scope thereof. Particular relationships, temperatures, pressures, and the like, are to be considered exemplary and not limitative of the overall scope of our process of producing isoamylenes, or isoprene, from a mixed butenes feed.

EXAMPLE I
Using Catalytic Cracker Butylenes

| Component | Feed (1) | Raffinate (5) | Recycle (14) | Total Triolefin Feed (14+5) | Triolefin Effluent (8) |
|---|---|---|---|---|---|
| Ethylene | — | — | — | — | — |
| Isobutene | 100[1] | 95 | 115 | 210 | 115 |
| Butene-1 | 80 | — | — | — | — |
| Butene-2 | 155 | 145 | 65 | 210 | 115 |
| Propylene | — | — | — | — | 71 |
| Isoamylenes+ | — | — | — | — | 119[2] |
| Total | 335 | 240 | 180 | 420 | 420 |

[1] All values in MT/day, metric tons per day.
[2] 80% by weight isoamylenes.

Catalytic cracker butylenes contain more butene-2 than is needed in the triolefin process. Therefore, a net yield of 50 metric tons/day of butene-2 results with production of 119 metric tons/day of isoamylenes of about 80 weight percent purity.

EXAMPLE II
Using Naphtha Cracker Butylenes

| Component | Raffinate (5) | Recycle (14) | Triolefin Feed (11+5) | Triolefin Effluent (8) |
|---|---|---|---|---|
| Ethylene | — | — | — | 55 |
| Propylene | — | 85 | 85 | 85 |
| Isobutylene | 125[1] | 150 | 275 | 150 |
| Butene-1 | — | — | — | — |
| Butene-2 | 75 | 90 | 165 | 90 |
| Isoamylenes + | — | — | — | 145[2] |
| Total | 200 | 325 | 525 | 525 |

[1] All values in MT/D, metric tons per day.
[2] 80% by weight isoamylenes.

Naphtha cracker butylenes contain less butene-2 than catalytic cracker butylenes requiring recycle of propylene, and may also require further imput of outside propylene.

These exemplary examples further illustrate our invention as a method of preparing isoamylenes from a mixed butenes feed. Such isoamylenes are useful as components in high-octane fuel synthesis. Or, the isoamylenes can be readily converted to isoprene for the manufacture of valuable polyisoprene rubbers.

The disclosure, including data, has illustrated the value and effectiveness of our invention. The examples, knowledge and background of the invention, and the general principles of chemistry, and of other applicable sciences, have formed the bases for which the broad descriptions of the invention, including the ranges of conditions and operant components have been developed, and have formed the bases for our claims here appended.

We claim:

1. A method of preparation of isoamylenes from a mixed butenes feed stream comprising butene-1, butenes-2, and isobutene, wherein said process comprises the steps:
    (a) contacting said mixed butenes stream with molecular sieve separation means whereby said butene-1 is substantially adsorbed and said butenes-2 and isobutene pass therethrough as a raffinate,
    (b) disproportionating said raffinate of isobutene and butenes-2 which can futher contain propylene in an effective disproportionation mole ratio of butenes-2 and isobutene, thereby forming a stream comprising isoamylenes, unconverted butenes-2, isobutene, propylene, and which can contain ethylene, wherein said mole ratio is about 1:1 isobutene: butenes-2 plus propylene where employed
    (c) separating said stream comprising isoamylenes into streams comprising propylene, butenes-2 and isobutene, said isoamylenes, and optionally an ethylene stream when said isoamylene stream further contains said ethylene,
    (d) recycling said separated butenes-2 and isobutenes to said disproportionating step,
    (e) desorbing said adsorbed butene-1, thereby producing a desorbed butene-1 stream,
    (f) isomerizing said desorbed butene-1 stream at least in part to at least one of further butenes-2, or isobutene, or both, so as to provide an effective mole ratio of butenes-2: isobutene for said step (b) in combination with butenes-2 and isobutene from said mixed feed,
    (g) recycling said further butenes-2, isobutene, or both, and any unconverted butene-1, to said molecular sieve separation step,
    (h) dimerizing as necessary at least a proportion of said ethylene when present to produce a dimerized steam of additional butenes and cycling said additional butenes to said step (a), wherein said ethylene dimerization assists in maintaining a proper butenes-2: isobutene disproportionation mole ratio for said step (b) thereby providing a method of preparation of isoamylenes from a mixed butenes feed stream providing for internal adjustments in order to provide for a balanced mole ratio for said disproportionation step (b).

2. The process according to claim 1 wherein said step (c) separating of said stream of isoamylenes is by fractionation means.

3. The process according to claim 1 comprising the further step of oxidatively dehydrogenating said isoamylenes, thereby converting said isoamylenes at least in part to isoprene.

4. The process according to claim 1 wherein said adsorbed butene-1 is desorbed, thereby producing a butene-1 stream, at least a portion of said butene-1 is double bond isomerized to butene-2, a further portion of said butene-1 is skeletally isomerized to isobutene, said butene-2 and isobutene, together with any unconverted butene-1, are recycled to said mixed butenes molecular sieve separation step.

5. The process according to claim 2 wherein said isoamylenes separation step comprises a substep process wherein said isoamylene stream from said disporportionation step is debutanized thereby removing said isoamylenes as a bottoms stream, and said propylene, isobutene, butene-2, and ethylene are removed overhead as a substantially isoamylenes-free stream,     wherein said isoamylenes-free stream thereafter is deethanized whereby said ethylene is removed as an ethylene overhead stream, thereby leaving a stream comprising butenes-2, isobutene, and propylene,     wherein said stream comprising butenes-2, isobutene, and propylene is in part depropanized to remove at least a portion of said propylene, leaving unconverted isobutene and butenes-2 wherein said unconverted isobutene and butene-2 are recycled to said disproportionation step, and     wherein the remaining part of said stream comprising isobutene, butenes-2, and propylene stream not subjected to said propylene fractionation substep, is recycled to said disproportionation step.

6. The process according to claim 1 wherein said molecular sieves comprise Type X or Type Y zeolites, and said molecular sieve contacting is conducted at a temperature in the range of about 50° to 150° F., at a pressure of about 200 to 250 psig.

7. The process according to claim 6 wherein said disproportionation step is conducted at a temperature in the range of about 650° to 750° F., at a pressure in the range of about 200 to 350 psig, employing a weight/weight/hour space velocity in the range of about 50 to 200.

8. The process according to claim 5 wherein said debutanizing substep is conducted at a top temperature of about 170° F, a bottom temperature of about 314° F., and employing a pressure of about 220 psia.

9. The process according to claim 5 wherein said deethanizing substep is conducted at a top temperature of about −11° F, a bottom temperature of about 203° F, and employing a pressure of about 340 psia.

10. The process according to claim 5 wherein said depropanizing substep is conducted at a top temperature of about 113° F., a bottom temperature of about 200° F., and employing a pressure of about 274 psia.

11. The process according to claim 5 wherein said double bond isomerization conversion step of butene-1 to butenes-2 employs a catalyst comprising ruthenium oxide associated with a suitable support material selected from silica, silica-alumina, alumina and titania, a conversion temperature in the range of about 200° to about 700° F., and a conversion pressure in the range of about 0 to 2,000 psig.

12. The process according to claim 5 wherein said skeletal isomerization conversion step for said butene-1 to isobutene employs a zirconium oxide or compound convertible to zirconium oxide upon calcination promoted with a halogen compound, at a contacting temperature in the range of about 400° to 1200° F., and at a pressure of atmospheric to about 200 psig.

13. The process according to claim 1 wherein said disproportionating step of said butenes-2 and isobutene to said isoamylenes employs a catalyst selected from the group consisting of (I) silica or thoria promoted by an oxide or a compound convertible thereto on calcination of tungsten, molybdenum, rhenium, or tellurium, or by sulfide of tungsten or molybdenum,     or (II) aluminum phosphate, zirconium phosphate, calcium phosphate, magnesium phosphate, or titanium phosphate, promoted by at least one of a sulfide of molybdenum or tungsten or by an oxide or a compound convertible thereto on calcination of molybdenum, tungsten, or rhenium, or by magnesium tungstate or beryllium phosphotungstate,     employing a contacting temperature in the range of about 200° F. to 350° F., a pressure in the range of about 200 to 350 psig, and a space velocity in the wt range of about 75 to 100.

14. The process according to claim 3 wherein said oxidative dehydrogenation of said isoamylenes to isoprene is conducted at a temperature in the range of about 700 to 1300 F., employing a pressure in the range of bout 0.1 to 250 psia, a space velocity in the range of about 50 to 5000 vapor V/Vol cat/hr, and employing a catalyst comprising an iron/phosphorus/oxygen catalyst system wherein the phosphorus represents about 0.01 to 2 times the stoichiometric amount required for orthophosphate relative to the iron.

15. The process according to claim 2 wherein said process comprises the further step of dimerizing said ethylene to a dimerized stream comprising butene-1, butenes-2, and isobutene, employing a catalyst comprising a reaction product of cobalt acetylacetonate and diethylethoxy-aluminum, a contacting temperature of 0° to 200° C., and a pressure of about 500 to 800 psig,     and wherein said so-produced ethylene dimers are recycled to said molecular sieve separation step.

16. A method of preparation of isoprene from a mixed butenes stream comprising butene-1, butenes-2, and isobutene, wherein said process comprises the steps:

(a) contacting said mixed butenes stream with molecular sieve separation means whereby said butene-1 is substantially adsorbed and said butenes-2, and isobutene pass therethrough as a raffinate stream,     (b) disproportionating said raffinate stream of isobutene and butenes-2 which can further contain propylene in an effective disproportionation mole ratio of isobutene:butenes-2, thereby forming an isoamylenes stream comprising isoamylenes, unconverted butene-2, isobutene, propylene, and ethylene when present, wherein said mole ratio is about 1:1 isobutene: butenes-2 plus propylene where employed     (c) separating said isoamylenes stream into streams comprising a propylene stream, an ethylene stream when said ethylene is present, separated butenes-2 and isobutene, and said isoamylenes,     (d) oxidatively dehydrogenating said isoamylenes to said isoprene,     (e) recycling said separated butenes-2 and isobutene to said disproportionation step (b),     (f) desorbing said adsorbed butene-1, thereby producing a butene-1 extract stream,     (g) double bond isomerizing at least a portion of said butene-1 to further butenes-2,     (h) skeletally isomerizing a further portion of said butene-1 to further isobutene, and (i) recycling said further butenes-2 and isobutene, and any unconverted butene-1, to said mixed butenes molecular sieve separation step (a), and (j) dimerize as necessary at least a proportion of said ethylene when present to produce a dimerized steam of additional butenes and cycling said additional butenes to said step (a), wherein said ethylene dimerization assists in maintaining a proper butenes-2:isobutene ratio for said step (b), and (k) recycling as necessary at least a portion of said propylene from said step (c) to supplement said butenes-2 in order to maintain an effective disproportionation ratio of butene-2 plus propylene:isobutene for said disproportionating step (b), thereby providing a method of preparation of isoprene from a mixed butenes feed stream providing for internal process balancing to provide for a balanced mole ratio for said disproportionation step (b).

17. The process according to claim 16 wherein said isoamylenes separation step (c) comprises a three sub-step process:
(da) αebutanizing said isoamylenes stream, thereby separating said isoamylenes as a bottoms stream, and said propylene, isobutene, butenes-2, and ethylene as an overhead substantially isoamylenes-free stream,
(db) fractionating said substantially isoamylenes-free stream into an overhead ethylene stream, and a bottoms stream comprising butenes-2, isobutene, and propylene,
(dc) fractionating at least a portion of said stream comprising butenes-2, isobutene, and propylene, thereby recovering a propylene stream and a stream containing unconverted isobutene and butenes-2.

18. The process of claim 17 wherein said unconverted isobutene and butenes-2 are recycled to said disproportionation step, and recycling
any said isobutene, butenes-2, and propylene stream not subjected to said fractionation substep (dc) to said disproportionation step (b).

19. The process according to claim 18 wherein said step (a) molecular sieves comprise Type X and Type Y zeolites, and said molecular sieve contacting is conducted at a temperature in the range of about 50° to 150° F., at a pressure of about 200 to 250 psig.

20. The process according to claim 19 wherein said disproportionation step (b) employs a catalyst selected from the group consisting of (I) silica or thoria promoted by an oxide or a compound convertible thereto on calcination of tungsten, molybdenum, rhenium, or tellurium, or a sulfide of tungsten or molbdenum, or (II) aluminum phosphate, zirconium phosphate, calcium phosphate, magnesium phosphate, or titanium phosphate, promoted by at least one of a sulfide of molybdenum or tungsten or by an oxide or a compound convertible thereto on calcination of molybdenum, tungsten, or rhenium, or by magnesium tungstate or beryllium phosphotungstate at a temperature in the range of about 650° to 750° F., a pressure in the range of about 200 psig to 350 psig, and a weight/weight/hour space velocity in the range of about 75 to 100;
wherein said double bond isomerization conversion step (g) of butene-1 to butenes-2 employs a catalyst comprising ruthenium oxide associated with a suitable support material selected from silica, silica-alumina, alumina and titania, employing a conversion temperature in the range of about 200° to about 700° F. at a pressure in the range of about 0 to 2,000 psig;
wherein said sketetal isomerization conversion step (h) of butene-1 to isobutene employs a zirconium oxide, or compound convertible to zirconium oxide upon calcination, or zirconium oxide promoted with a halogen compound represented by $ZrOx_2$ wherein $x$ is fluoride, bromide, chloride, or iodide, on alumina, at a contacting temperature in the range of about 400° to 1200° F., at a pressure in the range of atmospheric to about 200 psig; and
wherein said oxidative dehydrogenation step (d) of said isoamylenes to isoprene employs a temperature in the range of about 750° F to 1300° F., a pressure in the range of about 0.1 to 250 psia, a space velocity in the range of about 50 to 5000 vapor/vol/cat./hr., and a catalyst comprising iron/phosphorus/oxygen.

21. The process according to claim 20 comprising the further steps of
dimerizing said ethylene to a dimerized stream comprising butene-1 and butenes-2, employing a dimerizing temperature of about 0° C. to 200° C., and a pressure of about 500 to 800 psig and
recycling said so-produced ethylene dimers comprising butene-1 and butenes-2 -to said molecular sieve separation step.

22. The process according to claim 16 wherein said step (b) employs propylene as well as said butenes-2 and isobutene, and employs a mole ratio of about 1:1 isobutene:butene-2 plus propylene.

* * * * *